United States Patent [19]

Gohlke

[11] 4,177,288
[45] Dec. 4, 1979

[54] COMPOSITION FOR CONTROLLING FUNGI

[75] Inventor: Arthur F. Gohlke, Atlanta, Ga.

[73] Assignee: Cities Service Company, Tulsa, Okla.

[21] Appl. No.: 937,392

[22] Filed: Aug. 28, 1978

Related U.S. Application Data

[63] Continuation-in-part of Ser. No. 798,725, May 19, 1977, abandoned.

[51] Int. Cl.² .................................................. A01N 9/02
[52] U.S. Cl. ................................... 424/294; 424/304; 424/164
[58] Field of Search ...................... 424/294, 304, 164

[56] References Cited

U.S. PATENT DOCUMENTS

| 3,262,846 | 7/1966 | Ercegovich | 424/294 |
| 3,331,735 | 7/1967 | Battershell et al. | 424/304 |
| 3,456,055 | 7/1969 | Galloway | 424/304 |

Primary Examiner—V. D. Turner
Attorney, Agent, or Firm—Donald L. Traut

[57] ABSTRACT

A fungicidal composition comprising from 19 wt % to about 50 wt % of a halogenated aromatic dinitrile, from 19 wt % to about 50 wt % of copper salts of fatty and rosin acids, from about 0.05 wt % to about 15 wt % surfactant, and from about 2 wt % to about 60 wt % carrier. The copper salts comprise from about 20 wt % to about 30 wt % copper oleate, from about 15 wt % to about 25 wt % copper linoleate, from about 45 wt % to about 55 wt % copper abietate, and from about 1 wt % to about 2 wt % copper palmitate and copper stearate.

7 Claims, No Drawings

COMPOSITION FOR CONTROLLING FUNGI

This is a continuation-in-part application of application Ser. No. 798,725 filed May 19, 1977, now abandoned.

BACKGROUND OF THE INVENTION

This invention relates to a novel composition for use as a fungicide on plants. More particularly, this invention relates to fungicidal compositions containing as the active agent, an effective amount of a halogenated aromatic dinitrile and copper salts of fatty and rosin acids, and to the use of such compositions for retarding undesirable biological growth.

The fungicidal properties of halogenated aromatic dinitriles are well known. A particular prior art fungicidal composition is illustrated by U.S. Pat. Nos. 3,331,735 and 3,290,353, issued July 18, 1967 and Dec. 6, 1966, respectively, which are incorporated by reference. The patents cover a fungicidal and bactericidal composition comprising:

(a) from 1 to 99% of a halogenated aromatic dinitrile having the structure

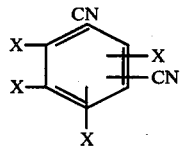

wherein each X is selected from a group consisting of hydrogen, chlorine, fluorine and bromine with at least one X being other than hydrogen, (b) from 0.05 to 1% surface-active agent, and (c) the balance an inert solid carrier.

The fungicidal properties of copper and copper salts are also well known. A prior art fungicidal composition is revealed in U.S. Pat. No. 3,262,846, issued July 26, 1966 which is incorporated by reference. U.S. Pat. No. 3,262,846 covers a fungicidal composition consisting essentially of 40 to 50 parts of copper salts of fatty and rosin acids, from 10 to 15 parts of a nonionic emulsifier and 25 to 40 parts of petroleum distillate boiling in the range of from 315° C. to 480° C. The salts include copper oleate, copper linoleate and copper abietate.

SUMMARY OF THE INVENTION

It is therefore an object of my invention to provide a novel composition which provides improved results over the prior art for the control of fungal growth on plants.

These and other objects will become apparent to those skilled in the art as the following description proceeds.

Broadly, this invention is a fungicidal and bactericidal composition which comprises a halogenated aromatic dinitrile, copper salts of fatty and rosin acids, a surfactant and a carrier. Secondly, this invention comprises the application of the aforesaid composition to plants for controlling bacteria and fungi.

DETAILED DESCRIPTION OF THE INVENTION

The composition of matter in this invention is a fungicidal compound which comprises, in combination, from 19 wt % to about 50 wt % of a halogenated aromatic dinitrile having the structure

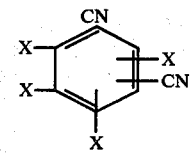

wherein each X is selected from a group consisting of hydrogen, chlorine, fluorine and bromine with at least one X being other than hydrogen, from 19 wt % to about 50 wt % of copper salts of fatty and rosin acids, from about 0.05 wt % to about 15 wt % surfactant, and from about 2 wt % to about 60 wt % carrier, said copper salts comprising from about 30 wt % to about 30 wt % copper oleate, from about 15 wt % to about 25 wt % copper linoleate, from about 45 wt % to about 55 wt % copper abietate and from about 1 to about 2 wt % copper palmitate and copper stearate.

A preferred formulation of this invention comprises from about 19 wt % to about 50 wt % halogenated aromatic dinitrile, from about 19 wt % to about 50 wt % copper salts, from about 0.05 wt % to about 15 wt % surfactant, and from about 2 wt % to about 60 wt % carrier. A more preferred formulation of this invention comprises from about 30 to about 40 wt % of a tetrachloroisophthalonitrile, from about 30 wt % to about 40 wt % copper salts, from about 5 wt % to about 10 wt % surfactant and from about 6 wt % to about 33 wt % carrier, said carrier selected from a group consisting of benzene, toluene, xylene, and trimethyl xylene. The most preferred composition comprises about 34.5 wt % of tetrachloroisophthalonitrile, about 35 wt % copper tallate, about 22 wt % trimethyl xylene and about 8.5 wt % surfactant, said surfactant comprising a 1:1 weight ratio of alkyl polyether alcohol and organic sulfonate.

The halogenated aromatic dinitriles useful in the present invention are more commonly designated in the art as phthalonitriles, isophthalonitriles, and terephthalonitriles. Compounds within this class, which are useful herein include tetrachloroterephthalonitrile, tetrafluoroterephthalonitrile, tetrachloroisophthalonitrile, difluorodichloroterephthalonitrile, 5-chloro-2,4,6-trifluoroisophthalonitrile, 2,3-dichloroterephthalonitrile, chlorotrifluoroterephthalonitrile, tetrafluoroterephthalonitrile, 4,6-dichloroisophthalonitrile, 2,4-dichloroterephthalonitrile, 2-chloroterephthalonitrile, 2-fluoroterephthalonitrile, tetrachlorophthalonitrile, 2-bromoterephthalonitrile, 2-chloro-3-fluoroterephthalonitrile, 2,3-difluoroterephthalonitrile, 2-chloro-5-fluoroterephthalonitrile, 2,5-difluoroteraphthalonitrile, 2,5-dibromoterephthalonitrile, 2,3,45-trichloroterephthalonitrile, dichlorodifluoroisophthalonitrile, trichlorofluoroisophthalonitrile, 4,6-difluoroisophthalonitrile, 4-bromoisophthalonitrile, tetrafluorophthalonitrile, 4-chloroisophthalonitrile, 3,4-dichlorophthalonitrile, chlorotrifluorophthalonitrile, dichlorodifluorophthalonitrile, trifluoroterephthalonitrile, 4-bromo-6-fluoroisophthalonitrile, 2-chloroisophthalonitrile, 4-chloroisophthalonitrile, 2,4-dichloroisophthalonitrile, 2-fluoroisophthalonitrile, 4-fluoroisophthalonitrile and 2-fluoro 4,5,6-trichloroisophthalonitrile. The more preferred dinitrile is tetrachloroisophthalonitrile.

The halogenated aromatic dinitriles of this invention generally may be prepared as described in U.S. Pat. Nos. 3,290,353 and 3,331,735. Typically, such preparations involve conversion of a ring-halogenated, i.e., chlorinated or brominated acid chloride to the corresponding ring-halogenated amide by treatment thereof with ammonia. The halogenated amide compound obtained is then dehydrated to give the desired chlorinated or brominated dinitrile. Alternatively, tetrahalogenated aromatic dinitriles may be prepared in good yield from the corresponding isomers by ammoxidizing the xylene to the dinitrile isomer, followed by vapor phase catalytic chlorination thereof. Additionally, it is also possible to prepare compounds of this invention by amidation of the corresponding halogenated dicarboxylic acid. The diamide obtained is then dehydrated to the desired halogenated dinitrile. The fluorinated dinitriles generally may be prepared from the chlorinated dinitriles by a halogen interchange whereby chlorine is replaced by fluorine. Typically, the chlorinated compound is reacted with an alkali metal fluoride, e.g. potassium fluroide.

While copper salts of fatty and rosin acids in general can be employed in this invention, such as those of fatty acids (containing from about 8 to 24 carbon atoms, preferably 12 to 18 carbon atoms) and rosin acids, the copper salts of tall oil fatty and rosin acids, such as copper tallate, are preferred.

The preferred copper tallate comprises a mixture of copper oleate about 20 to 30 wt %), copper linoleate (about 15 to 25 wt %) and copper abietate (about 45 to 55 wt %), and about 1 wt % to about 2 wt % copper palmitate and copper stearate. Copper salt mixtures will, by the nature of the production methods, contain additional copper salts of fatty acids such as minor amounts of copper palmetate and copper stearate.

Generally the copper salts of fatty and rosin acids included in the fungicidal composition contain about 4 wt % elemental copper. The preferred copper salt, copper tallate, contains about 4.1 wt % elemental copper.

The copper salts of rosin and fatty acids are prepared by reacting a heated mixture of commercially available fatty and rosin acids with copper hydroxide as described in U.S. Pat. No. 3,262,846.

In the practice of this invention, the composition of halogenated aromatic dinitriles and copper salts of rosin and fatty acids may be applied in undiluted form to the plant to be protected. It is frequently desirable, however, to apply them in admixture with either solid or liquid inert adjuvants. Thus, the compound can be applied to the plants for fungicidal purposes, for example, by spraying them with aqueous or organic solvent dispersions of these chemicals. The choice of an appropriate solvent for a liquid compound is determined largely by the concentration of active ingredient which is desirable to employ, by the volatility required in a solvent, the cost of the solvent and the nature of the material being treated.

Among the many suitable organic solvents which can be employed as carriers for the present fungicidal compound, there may be mentioned aromatic hydrocarbons such as benzene, toluene, o-xylene, m-xylene, p-xylene, hemimellitene, pseudocumene, mesitylene, prehnitene, isodurene, durene, pentamethylbenzene and hexamethylbenzene; ketones such as acetone, methyl ethyl ketone and cyclohexanone; chlorinated hydrocarbons such as chloroform; and esters such as ethyl acetate, amyl acetate and butyl acetate. It is preferred to employ an aromatic hydrocarbon selected from a group consisting of benzene, toluene, "xylene" (a mixture of o-xylene, m-xylene, and p-xylene), and "trimethyl xylene" (a xylene aromatic distillate cut having a closed cup TAG flash point of 40°–41° C.). As a matter of cost and lower volatility, xylene is a more preferred carrier, however since the Department of Transportation requires that the carrier flash point be in excess of 38° C. for interstate transportation, the more preferred carrier is trimethyl xylene.

The carrier, either liquid or solid, can be employed in varying amounts, but it is generally preferred to employ the carrier in amounts of from about 2 to about 60 wt % of the total composition. In more preferred embodiments, the carrier is an aromatic hydrocarbon selected from a group consisting of benzene, toluene, xylene, and trimethyl xylene, and is employed in amounts between about 6 and 33 wt %. Most preferably, trimethyl xylene is the aromatic hydrocarbon carrier of the fungicidal formulation and is in the amount of about 22 wt % of the formulation. Trimethyl xylene is of the purity generally designated as "agricultural grade" (boiling range of 137°–143° C.) and as such may contain small amounts of benzene, toluene and other material.

The solid form of the composition of halogenated aromatic dinitriles and copper salts of rosin and fatty acids can also be applied to plants along with inert solid adjuvants or carriers such as talc, pyrophyllite, kieselguhr, chalk diatomaceous earth, lime calcium carbonate, bentonite, fuller's earch, cottonseed hulls, wheat flour, soybean flour, pumice, tripoli, wood flour, walnut shell flour, lignin, etc.

It is frequently desirable to incorporate a surfactant in the bactericidal and funigicidal compositions of this invention. Such surfactants are advantageously employed in both the solid and liquid compositions. The surfactant can be anionic or nonionic in character or combinations thereof.

The anionic and nonionic surfactants that are employed in the present invention are well known, available commercially, and described in the literature. In general, any anionic and any nonionic surfactant can be employed that is compatible in the composition and will effect surface activity.

It is to be understood that more than one anionic or nonionic surfactant can be employed but it is preferred that at least one anionic and at least one nonionic surfactant be used in the formulation. The proportion of nonionic to anionic can vary, but in general will be between about ½ to 5 parts by weight of nonionic to 1 part by weight of anionic.

Nonionic surfactants are broadly categorized as including (a) ethoxylated alkylphenols, (b) ethoxylated aliphatic alcohols, (c) carboxylic esters, and (d) carboxylic amides. Among the nonionic surfactants that can be employed, the alkyl polyether alcohol, alkylaryl polyether alcohol, octylphenoxy polyethoxy ethanol, modified polyethoxylated straight-chain alcohol, polyoxyalkylated oleyl alcohol, and alkanolamide are preferred.

Anionic surfactants are broadly categorized as including (a) carboxylic acids and salts, (b) various sulfonic acids and salts (including alkylbenzene sulfonates, petroleum sulfonates, sulfosuccinates, naphthalene sulfonates, and substituted taurates, (c) sulfates and sulfated products (including sulfated alcohols, sulfated natural fats, sulfated acids, amides, and esters, and sulfated, ethoxylated alkylphenols and alcohols), and (d) phosphate esters. Among the anionic surfactants that can be employed, (a) sulfonic acids and their salts, such as amyl ester of sodium salt of sulfonated oleic acid, sodium alkylaryl sulfonate, sodium alkylaryl polyether sulfonate, petroleum sulfonate, sodium petroleum sulfonate and dioctyl sodium sulfosuccinate.

(b) sulfates such as sodium lauryl sulfate, sulfated castor oil, ali-phatic ester sulfate, sulfated ethoxylated alkylphenols such as sodium salt of a sulfate ester of an alkylphenoxy-poly (ethyleneoxy) ethanol, and sulfated ethoxylated alcohol such as an ammonium salt of a sulfated linear primary alcohol ethoxylate.

(c) phosphate esters such as organic phosphate ester are preferred.

A preferred formulation of the surfactant adjuvant includes a 1:1 weight ratio of anhydrous mixtures of the nonionic alkyl polyether alcohol and the anionic organic sulfonates, especially sodium alkylaryl sulfonate. Similarly, a blend of a nonionic alkylaryl polyether alcohol with anionic dioctyl sodium sulfosuccinate in a ratio of 3:1 respectively by weight, and a blend of the nonionic octyl phenoxy polyethoxy ethanol with the anionic sodium alkylaryl polyether sulfonate, in a ratio of from ⅛ to 5 parts of the nonionic to 1 part by weight of the anionic are also preferred. A more preferred blend of anionic and nonionic surfactants comprises about 3 parts of isooctyl phenyl polyether ethanol, the polyether group having 9 to 10 ethoxy groups, about 4 parts of isooctyl phenyl polyethoxy ethanol, the polyether group having 5 ethoxy groups, and about 2 parts by weight of dioctyl sodium sulfosuccinate. The above-mentioned surfactants, singly and in combination, are representative of suitable surfactants, and many other combinations will be evident to those skilled in the art.

For adjuvant purposes, a minor amount of the surfactant may be employed. If the surfactant is used only to impart wetting qualities, for example, to a spray solution, as little as 0.05 wt % of the spray solution, is preferred. The use of larger amounts of surfactants is not based upon wetting properties but is a function of the physiological behavior of the surfactant. These considerations are particularly applicable in the treatment of plants. In these applications, amounts of the surfactants up to 15 wt % are preferred. Amounts of the surfactants between about 5 to about 10 wt % are more preferably, with the most preferred composition containing about 8.5 wt % of surfactants.

The composition of the invention is compatible also with other agricultural chemical additives, especially wettable sulfur and minor amounts of other fungicides and bactericides. In a preferred embodiment, the weight ratio of wettable sulfur to composition is from about 0.833:1 to about 2.78:1.

A liquid formulation can be prepared by any suitable method. By way of illustration, the preferred composition is formed by first reacting heated tall oil rosin and fatty acids with copper hydroxide. This is accomplished by introducing copper hydroxide and a defoamer into a reactor while at the same time also introducing the heated tall oil acids, xylene and a small portion of the surfactants into the reactor. The copper salt component is withdrawn as a liquid from the bottom of the reactor, cooled, and tetrachloroisophthalonitrile, the remainder of the surfactants, and additional xylene, if needed, are added. Vapors withdrawn from the reactor are condensed and vented. The resulting liquid xylene, separated from the condensed vapor, is then recycled to the reactor or added to the fungicide formulation if needed.

For spray application, the active ingredients may be dissolved or dispersed in a liquid carrier, such as water or other suitable liquid. The active ingredients can be in the form of a solution, suspension, dispersion or emulsion in aqueous or nonaqueous medium.

Alternatively, the active ingredients in liquid form, including solutions, dispersions, emulsions and suspensions thereof may be admixed with the solid carrier in finely divided form in amounts small enough to preserve the free-flowing property of the final dust composition.

The composition may be applied to the foliage by any conventional method including spraying and overhead irrigation up to the day of the crop harvest. The application normally commences before the disease attacks or no later than at initial attack (but before spore germination) and is repeated at 7 to 14 day intervals. The application rate ranges from 1 to 20 pounds of the composition per acre diluted in water for adequate coverage. The application rate is dependent upon the type of crop, the degree of infection, and type of disease. The rate of spraying ranges from 1 to 7 pounds per acre for field and vegetables crops and 6 to 18 pounds per acre for citrus crops. Some of the food crops (and ornamentals) on which the formulations are recommended for application are:

Vegetables: potatoes, carrots, green beans, celery, beets, cucumbers, cantaloupes, squash, broccoli, pumpkins, watermelons, lettuce, onions, tomatoes and peppers Fruit: citrus, apples, pears, grapes, trailing berries, peaches, sour cherries, mangoes, and avocados Nuts: walnuts and pecans Field Crops: corn, wheat, alfalfa, oats, barley, rye, soybeans, colored and navy beans, peanuts, sugar beets, bananas, coffee, cotton, and rice Ornamentals: gladiolas, chrysanthemums, begonias, iris, azaleas, rhododendron, roses, ornamental foliage plants, pyracantha, juniper, pine and sycamore.

The composition is particularly useful on tomatoes for bacteria blight and late blight, on potatoes and celery for early and late blights, and on peanuts for Septoria leaf spot, rust and Webb blotch.

In order that those skilled in the art may more completely understand the present invention and the preferred methods by which the same may be carried into effect, the following examples are offered.

EXAMPLE 1

The following test measures the ability of the compositions of this invention to inhibit fungal growth. As compared to a control group and two commercial formulations the test composition was measured for the ability to protect tomato foliage against infection by the early blight (*Alternia solani*) and Septoria blight (*Septoria lycopercici*).

Test tomatoes were grown under normal commercial field conditions. Test sprays were applied from beginning of bloom through harvest. Both disease organisms infected the same plants, but effective control for each disease was rated separately which is possible due to different visual symptoms of each disease.

A first commercial formulation, containing two pounds of a composition consisting of 75 wt % tetrachloroisophthalonitrile and 25 wt % inerts [typically inerts would include a carrier diluent such as talc and a surfactant such as Aerosol OS (sodium salt of propylated napthylenesulfonic acid)] (Bravo 75 WP Diamond Shamrock Co.) mixed with 100 gallons of water, was applied at a rate of 100 gallons of solution per acre of tomatoes.

A second commercial formulation containing 4.046 pounds of a composition consisting of 48 wt % of copper salts of fatty and rosin acids, 9 wt % of a combination of an anionic surfactant and 43 wt % xylene (CITCOP 4E-Cities Service Company) mixed with 100 gallons of solution per acre of tomatoes. The copper salts comprise a mixture of about 29.5 wt % copper oleate, about 23.0 wt % copper linoleate, about 45.5 wt % copper abietate, and 2.0 wt % copper palmitate and copper stearate.

The test formulation of the present invention containing 3.023 pounds of a composition comprising 24.75 wt % tetrachloroisophthalonitrile, 32.01 wt % copper salts of fatty and rosin acids, 6.03 wt % of a combination of an anionic emulsifier and nonionic emulsifier, 28.94 wt % xylene and 8.27 wt % inerts [typically inerts would include a carrier diluent such as talc and a surfactant such as Aerosol OS (sodium salt of propylated napthylenesulfonic acid)] (the formulation being 1 pound of Bravo 75 WP and 2.023 pounds of CITCOP 4E) mixed with 100 gallons of water, was applied at a rate of 100 gallons per acre of tomatoes. The copper salts comprise a mixture of about 29.5 wt % copper oleate, about 23.0 wt % copper linoleate, about 45.5 wt % copper abietate, and 2.0 wt % copper palmitate and copper stearate.

After 45 days from the first application of the compounds, disease severity estimates were made on the leaves of the tomato plants. The data was converted to a severity scale of 0 for no disease to 5 for plants experiencing 90% defoliation. The converted results are shown in Table A for the control group, the two commercial preparations and the composition of the invention.

Types of treatment and severity estimates are given for both early blight and Septoria blight in Table A:

TABLE A

| Treatment | #active ingredient/acre | Disease Control Ratings | |
|---|---|---|---|
| | | Early Blight | Septoria leaf spot |
| Control (no fungicide or bactericide formulation or spray | 0.0 | 3.50 | 3.75 |
| Tetrachloroisophthalonitrile | 1.5 | 0.0 | 0.5 |
| Copper Salts | 1.94 | 1.5 | 1.5 |
| Applicant's composition | .75 (tetra) 0.97 (copper) | 0.0 | 0.0 |

The results shown in Table A illustrate that the novel composition is equal to or better than either the tetrachloroisophthalonitrile composition or the copper salt composition.

EXAMPLE II

The following example measured again the ability of the composition of this invention to inhibit bacterial and fungal growth as compared to a control group and two commercial formulation. The example followed the test procedures as outlined in Example I.

A first commercial formulation, containing 2.3 pounds of a composition consisting of 54 wt % tetrachloroisophthalonitrile and 46 wt % inerts (typically this would include a viscosity modifier such as kaoline clay, a surfactant such as Triton-155 produced by Rohn and Haas and water) (Bravo 6F-Diamond Shamrock Co.) mixed with 100 gallons of water, was applied at a rate of 100 gallons of solution per acre of tomatoes.

A second commercial formulation containing 4.046 pounds of a composition consisting of 48 wt % of copper salts of fatty and rosin acids, 9 wt % of a combination of an anionic surfactant and a non-ionic surfactant and 43 wt % xylene (CITCOP 4-E-Cities Service Company) mixed with 100 gallons of water, was applied at a rate of 100 gallons of solution per acre of tomatoes. The copper salts comprise a mixture of about 29.5 wt % copper oleate, about 23.0 wt % copper linoleate, about 45.5 wt % copper abietate, and 2.0 wt % copper palmitate and The test formulation of the present invention, containing 3.173 pounds of a composition comprising 19.6 wt % comprising tetrachloroisophthalonitrile, 30.6 wt % copper salts of fatty and rosin acids, 5.7 wt % of a combination of an anionic emulsifier and nonionic emulsifier, 27.4 wt % of xylene, and 16.7 wt % of inerts (typically this would include a viscosity modifier such as kaoline clay, a surfactant such as Triton-155 produced by Rohn and Haas and water) (the formulation being 1.15 pounds of Bravo 6-F and 2.023 pounds of CITCOP 4E), mixed with 100 gallons of water, was applied at a rate of 100 gallons per acre of tomatoes. The copper salts comprise a mixture of about 29.5 wt % copper oleate, about 23.0 wt % copper linoleate, about 45.5 wt % copper abietate, and 2.0 wt % copper palmitate and copper stearate.

The treatment was repeated every 6-15 days. After 7 treatments and 107 days, severity estimates were made on the leaves of the tomato plants. The data is shown in Table B:

TABLE B

| Treatment | #active ingredient/acre | Disease Control Ratings | |
|---|---|---|---|
| | | Early Blight | Septoria leaf spot |
| Control (no fungicide or bactericide formulation or spray | 0.0 | 3.5 | 3.0 |
| Tetrachloroisophthalonitrile | 1.242 | 0.87 | 0.75 |
| Copper Salts | 1.94 | 1.5 | 1.25 |
| Applicant's composition | 0.62 (tetra) 0.97 (copper) | 0.5 | 0.37 |

The results shown in Table B illustrate that the novel composition produces better results than attained by either the tetrachloroisophthalonitrile compound or the copper salt composition.

Other tests involving cabbages, potatoes, celery and peanuts using the novel composition produce similar results.

Trimethyl xylene may be substituted for xylene and similar results will be found.

I claim:

1. A fungicide composition comprising, in combination, from about 19 wt % to about 50 wt % of a halogenated aromatic dinitrile having the structure

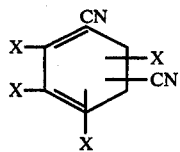

wherein each X is selected from the group consisting of hydrogen, chlorine, fluorine and bromine with at least one X being other than hydrogen; from about 19 wt % to about 50 wt % of copper salts of fatty and rosin acids, from about 0.05 wt % to about 15 wt % surfactant, and from about 2 wt % to about 60 wt % carrier, said copper salts comprising from about 20 wt % to about 30 wt % copper oleate, from about 15 wt % to about 25 wt % copper linoleate, from about 45 wt % to about 55 wt % copper abietate, from 1 wt % to about 2 wt % copper palmitate and copper stearate.

2. The composition of claim 1 comprising from about 30 to about 40 wt % of tetrachloroisophthalonitrile, from about 30 to about 40 wt % copper salts, from about 5 to about 10 wt % surfactant, and from about 6 wt % to about 33 wt % carrier, said carrier selected from the group consisting of benzene, toluene, xylene, and trimethyl xylene.

3. The composition of claim 2 wherein said carrier is trimethyl xylene.

4. The composition of claim 2 comprising about 34.5 wt % of tetrachloroisophthalonitrile, about 35 wt % copper tallate, about 22 wt % trimethyl xylene and about 8.5 wt % surfactant, said surfactant comprising a 1:1 wt ratio of alkyl polyether alcohol and organic sulfonate.

5. The composition of claim 4 additionally containing finely divided sulfur dispersed therein in ratio of sulfur to composition of from about 0.833:1 to about 2.78:1.

6. A method of controlling fungi which comprises contacting the fungi with an effective amount of a composition of from 10 to about 60% of a halogenated aromatic dinitrile having the structure

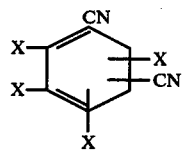

wherein each X is selected from the group consisting of hydrogen, chlorine, fluorine and bromine with at least one X being other than hydrogen; from 10 to 60% of copper salts of fatty and rosin acids, a minor amount of a surfactant and the balance a carrier.

7. The method of claim 6 wherein said composition comprises from about 19 wt % to about 50 wt % halogenated aromatic dinitrile, from about 19 wt % to about 50 wt % copper salts, from about 0.05 wt % to about 15 wt % surfactant, and from about 2 wt % to about 60 wt % carrier.

* * * * *